US009475952B2

(12) United States Patent
Jelonek et al.

(10) Patent No.: US 9,475,952 B2
(45) Date of Patent: *Oct. 25, 2016

(54) REVERSIBLE COLOR-CHANGING INK FORMULATIONS AND NONWOVEN WIPES

(71) Applicant: Illinois Tool Works, Inc., Glenview, IL (US)

(72) Inventors: Paul Richard Jelonek, Geneva, IL (US); Emani Bernardo, Schaumberg, IL (US)

(73) Assignee: Illinois Tool Works Inc., Glenview, IL (US)

( * ) Notice: Subject to any disclaimer, the term of this patent is extended or adjusted under 35 U.S.C. 154(b) by 45 days.

This patent is subject to a terminal disclaimer.

(21) Appl. No.: 14/284,910

(22) Filed: May 22, 2014

(65) Prior Publication Data

US 2014/0256053 A1 Sep. 11, 2014

Related U.S. Application Data

(63) Continuation of application No. 12/905,816, filed on Oct. 15, 2010, now Pat. No. 8,772,185.

(51) Int. Cl.
| | |
|---|---|
| *A47L 13/17* | (2006.01) |
| *C09D 11/00* | (2014.01) |
| *C09D 11/50* | (2014.01) |
| *C11D 17/04* | (2006.01) |
| *D06P 1/00* | (2006.01) |
| *D06P 1/52* | (2006.01) |
| *D06P 1/651* | (2006.01) |
| *G01N 31/22* | (2006.01) |

(52) U.S. Cl.
CPC ............... *C09D 11/50* (2013.01); *A47L 13/17* (2013.01); *C11D 17/049* (2013.01); *D06P 1/00* (2013.01); *D06P 1/525* (2013.01); *D06P 1/5264* (2013.01); *D06P 1/5278* (2013.01); *D06P 1/5285* (2013.01); *D06P 1/65168* (2013.01); *D06P 1/65193* (2013.01); *G01N 31/22* (2013.01); *Y10T 436/173845* (2015.01); *Y10T 442/20* (2015.04); *Y10T 442/2525* (2015.04)

(58) Field of Classification Search
CPC ..... A47L 13/17; C09D 11/50; C09D 17/049; D06P 1/00; D06P 1/525; D06P 1/5264; D06P 1/5278; D06P 1/5285; D06P 1/65168; D06P 1/65193; G01N 31/22; Y01T 436/173845; Y01T 442/20; Y01T 442/2525
See application file for complete search history.

(56) References Cited

U.S. PATENT DOCUMENTS

| | | | |
|---|---|---|---|
| 4,311,479 A | 1/1982 | Fenn et al. | |
| 4,678,704 A | 7/1987 | Fellows | |
| 5,432,000 A * | 7/1995 | Young, Sr. | ............ A61F 13/511 428/357 |
| 5,503,076 A | 4/1996 | Yeo | |
| 5,580,578 A | 12/1996 | Oshlack et al. | |
| 5,948,605 A | 9/1999 | Wang et al. | |
| 5,962,001 A | 10/1999 | Rose et al. | |
| 6,017,869 A | 1/2000 | Lu et al. | |
| 6,312,484 B1 | 11/2001 | Chou et al. | |
| 6,399,560 B1 * | 6/2002 | Kwon | ..................... A01N 43/40 510/130 |
| 6,794,318 B2 | 9/2004 | Anderson et al. | |
| 7,015,156 B2 | 3/2006 | Maldonado et al. | |
| 7,314,752 B2 | 1/2008 | Kritzman et al. | |
| 8,080,704 B2 | 12/2011 | Uchida et al. | |
| 8,772,184 B2 * | 7/2014 | Farrugia | ................ A01N 25/34 442/123 |
| 8,772,185 B2 * | 7/2014 | Jelonek | ................... A47L 13/17 424/10.3 |
| 8,772,186 B2 * | 7/2014 | Farrugia | ................ A01N 25/34 442/123 |
| 2001/0031595 A1 | 10/2001 | Anderson et al. | |
| 2002/0108640 A1 | 8/2002 | Barger et al. | |
| 2004/0038848 A1 | 2/2004 | Kritzler | |
| 2004/0209539 A1 | 10/2004 | Confalone et al. | |
| 2006/0283746 A1 | 12/2006 | Sutoh et al. | |
| 2006/0293205 A1 | 12/2006 | Chung | |
| 2007/0238190 A1 | 10/2007 | Klei et al. | |
| 2007/0238831 A1 | 10/2007 | Klei et al. | |
| 2008/0057532 A1 * | 3/2008 | Martin | .................... A61L 15/56 435/34 |
| 2010/0247371 A1 * | 9/2010 | Farrugia | ................ A01N 25/34 422/3 |
| 2012/0093736 A1 | 4/2012 | Jelonek et al. | |
| 2013/0104325 A1 | 5/2013 | Farrugia et al. | |

FOREIGN PATENT DOCUMENTS

| | | |
|---|---|---|
| CN | 1260011 A | 7/2000 |
| CN | 1429085 A | 7/2003 |
| CN | 1529564 A | 9/2004 |
| CN | 1625379 A | 6/2005 |
| CN | 1758926 A | 4/2006 |
| CN | 1878835 A | 12/2006 |
| CN | 101330896 A | 12/2008 |

(Continued)

OTHER PUBLICATIONS

H. Starp et al., "Novel teststrip with increased accuracy," Fresenius J., Anal Chem (2000), 368, pp. 203-207.
T. Werner et al., "Ammonia-sensitive Polymer Matrix Employing Immobilized Indicator Ion Pairs," Analyst, Jun. 1995, vol. 120, pp. 1627-1631.
W. Wroblewski et al., "Cellulose based bulk pH optomembranes," 1998 Elsevier Science S.A., B 48, pp. 471-475.

(Continued)

*Primary Examiner* — Abigail Fisher
(74) *Attorney, Agent, or Firm* — Maxwell J. Petersen; Lewis, Brisbois, Bisgaard & Smith

(57) ABSTRACT

A reversible color-changing polymeric article includes a polymeric material and a dried reversible color-changing ink formulation durably bound to the polymeric material. During use, the polymeric article is impregnated with a sanitizer solution that contains a quaternary ammonium compound. The polymeric article reversibly changes between a first color when impregnated with the sanitizer solution and a second color when the sanitizer solution is depleted during use.

18 Claims, 1 Drawing Sheet

(56) References Cited

FOREIGN PATENT DOCUMENTS

| EP | 2 067 458 A1 | 6/2009 |
|----|----|----|
| JP | 60-178362 | 9/1985 |
| JP | 05-154077 | 6/1993 |
| WO | WO 01/87132 A1 | 11/2001 |
| WO | WO 2010/079098 A1 | 7/2010 |

OTHER PUBLICATIONS

Co-pending U.S. Appl. No. 14/284,866, filed May 22, 2014; inventors Darren J. Farrugia et al.; title Reversible Color-Changing Sanitizer-Indicating Nonwoven wipe.

* cited by examiner

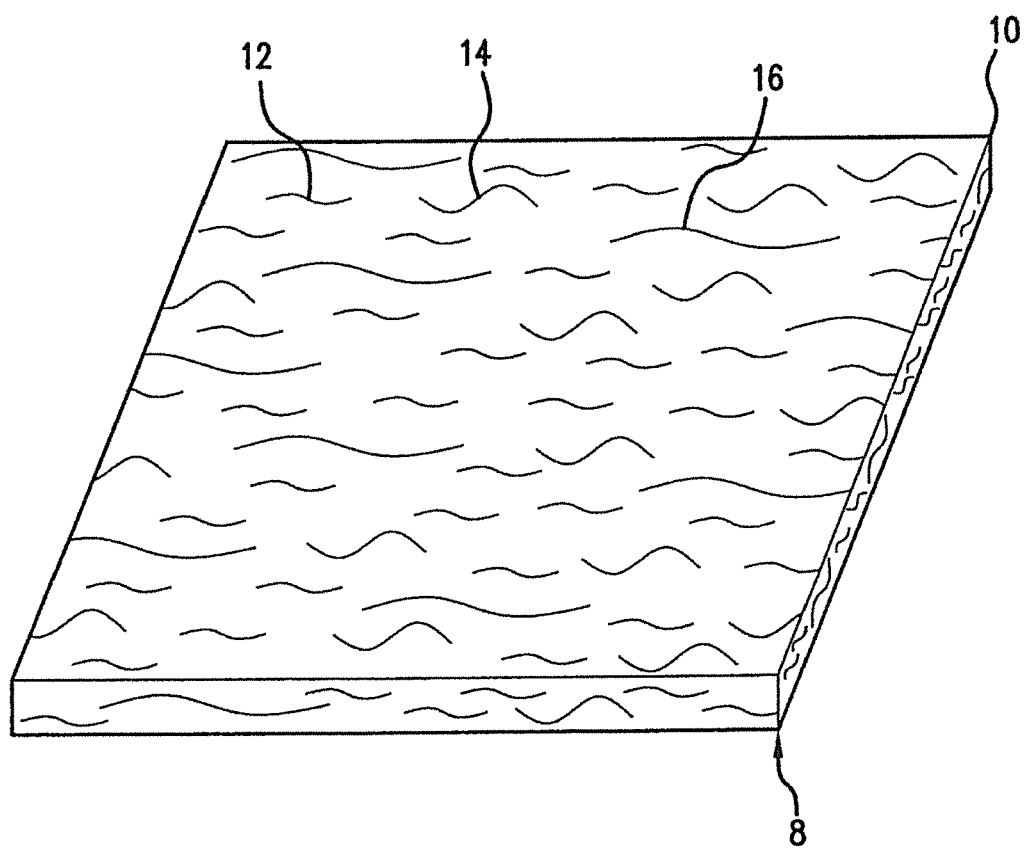

REVERSIBLE COLOR-CHANGING INK FORMULATIONS AND NONWOVEN WIPES

CROSS REFERENCE TO RELATED APPLICATIONS

This application is a continuation of U.S. patent application Ser. No. 12/905,816, filed on 15 Oct. 2010, the contents of which are incorporated by reference in their entirety and made a part thereof.

FIELD OF THE INVENTION

The present invention is directed to a color-changing ink formulation and nonwoven wipe for use with a sanitizer solution. The color changes from a first color to a second color when a concentration of sanitizer in the nonwoven wipe falls below a threshold level, and changes from the second color back to the first color when the concentration of sanitizer is again raised above the threshold level, for repeated cycles of use.

BACKGROUND OF THE INVENTION

Fabric wipes having color indicators are disclosed in U.S. Pat. No. 4,311,479, issued to Fenn et al., and in U.S. Pat. No. 4,678,704, issued to Fellows. Fenn et al. discloses a cloth impregnated with an antimicrobial composition that is activated upon contact with a liquid such as water, and is ionically bonded to the cloth. Small portions of the impregnated cloth are dyed with an indicator dye which bonds preferentially to the antimicrobial composition so that when the antimicrobial composition is exhausted, the dye will disappear from the cloth.

Fellows discloses an impregnated fabric material having an active cationic impregnant bonded to its fabric substrate. An anionic indicator dye in combination with a further cationic component is also bonded to the substrate. The dye bonds to the further cationic component more readily than to the substrate and the further cationic component competes with the impregnant for bonding to the dye. In the case of a wiping cloth, when the dye has been removed to indicate exhaustion of the active component, enough active component remains on the cloth to provide a safety margin.

These and similar prior art fabrics had color indicators to indicate the dissipation of impregnant. Yet the indicators only worked once, and only changed color once. If the fabric was then recharged with impregnant, such as by dipping it into a bucket, the original color would not return and the indicator function would not return.

Co-pending U.S. patent application Ser. No. 12/702,138 to Farrugia et al., filed on 8 Feb. 2010, addresses this problem to some degree by providing a reversible color-changing sanitizer indicator. The reversible color-changing ink formulation includes about 10-50% by weight of a polymer binder, about 10-50% by weight of a wetting agent, about 0-10% by weight of an ionic stabilizer, and about 1-10% by weight of an anionic indicator compound, based on a dry weight of the ink formulation. The color-changing ink formulation is bound to the nonwoven fabric wipe using the polymer binder. Suitable polymer binders include cellulose acetate and cellulose acetate derivatives.

While polymer binder concentrations near the high end of the range described in Farrugia may increase the binding properties of the ink formulation, they also diminish or dilute the color provided by the ink formulation. There is a need or desire for a reversible color-changing ink formulation and nonwoven wipes that can utilize a higher amount of other polymer binders and thus provide more durable binding, while providing sufficient color.

SUMMARY OF THE INVENTION

The present invention is directed to a reversible color-changing ink formulation and nonwoven wipes impregnated with it. The reversible color-changing ink formulation includes a higher amount of polymer binder, and has a composition that provides sufficiently acute color notwithstanding the higher concentration of binder. The improved reversible color-changing ink formulation provides more durable binding to the nonwoven wipes to which it is applied. Accordingly, the nonwoven wipes are potentially capable of reversibly changing color for a higher number of cycles during use.

The nonwoven wipe can be used to wipe down tables and countertops, for example, until the concentration of sanitizer in the wipe falls below a threshold concentration. At that point, the color of the nonwoven wipe changes from a first color to a second color. The nonwoven wipe can then be recharged, for example by immersing it in a bucket of sanitizer solution. The recharged nonwoven wipe then changes back to the first color, and can be used until the concentration of sanitizer falls to the threshold concentration and the color again changes to the second color. The nonwoven wipe is recharged again, and the cycle is repeated until the nonwoven wipe becomes exhausted due to soiling or damage, or the cleaning task is completed.

The nonwoven wipe includes a cloth-like nonwoven fabric formed, at least in part, of absorbent nonwoven fibers formed from cellulose or another suitable material. The absorbent fibers can be formed from rayon. The nonwoven fibers can be used alone or in combination with reinforcing nonwoven fibers, which need not be absorbent. The structural fibers can be formed of polyester or another suitable material.

The cloth-like nonwoven fabric is coated with an improved reversible color-changing ink formulation that durably binds itself to the nonwoven fabric, and remains bound during repeated use cycles. The reversible color-changing ink formulation includes about 55-98% by weight of a polymer binder, about 0.1-20% by weight of a reversible color-changing dye, zero to about 40% by weight of a plasticizer, zero to about 30% by weight of a particulate inorganic filler, and zero to about 30% by weight of a color brightener, based on dry weight of the ink formulation. The ingredients of the ink formulation are dissolved or dispersed in an organic or inorganic solvent for application to a cloth-like nonwoven fabric. The cloth-like nonwoven fabric may be cut and converted into individual nonwoven wipes before or after the reversible color-changing ink formulation is applied and dried. When fully dried, the reversible color-changing ink formulation does not leach or otherwise escape from the nonwoven wipe, and can reversibly change color in response to a change in concentration of sanitizer in the nonwoven wipe.

The nonwoven wipe is impregnated with a sanitizer, suitably one that is based on a quaternary ammonium compound. The nonwoven wipe may be provided with the sanitizer already impregnated. Alternatively, the nonwoven wipe may be provided without sanitizer, and may be impregnated with sanitizer by the user. In a preferred embodiment, the desired minimum concentration of quaternary ammonium compound in the nonwoven wipe (which causes color change) may range from about 180 ppm to about 250 ppm, based on the dry weight of the nonwoven wipe. The nonwoven wipe is impregnated with a higher amount of quaternary ammonium compound, as explained below. When the concentration of quaternary ammonium compound falls to the threshold level during use, the resulting color change indicates the need to recharge. The quaternary ammonium compound is often provided in an aqueous solution, and can be applied by dipping the nonwoven wipe in a bucket containing the sanitizer solution. The cycle of impregnation followed by use can be repeated several times because the ink formulation is durably bound to the nonwoven wipe by the binder.

By reversibly changing color during use, the nonwoven wipe provides a reliable indication of when it needs to be recharged during use, due to depletion of the sanitizer. By recharging and maintaining proper sanitizer concentration, the nonwoven wipe can be used for as many impregnation and use cycles as are needed to complete the task at hand, or until the wipe becomes damaged or heavily soiled.

With the foregoing in mind, it is a feature and advantage of the invention to provide a nonwoven wipe having a reversible color-changing sanitizer indicator, which nonwoven wipe can be recharged and used several times while providing a reliable indication of sanitizer concentration.

It is also a feature and advantage of the invention to provide a nonwoven wipe having extended use life due to the presence of a durably bound ink formulation that repeatedly and reversibly indicates changes in sanitizer concentration in the nonwoven wipe.

BRIEF DESCRIPTION OF THE DRAWING

FIG. 1 is a perspective view of a nonwoven wipe according to the invention.

DETAILED DESCRIPTION OF THE INVENTION

Referring to FIG. 1, a reversible color-changing sanitizer indicating nonwoven wipe 8 of the invention is formed using a cloth-like nonwoven fabric 10 including a plurality of nonwoven fibers 12. The nonwoven fibers 12 include absorbent nonwoven fibers 14 and may optionally include reinforcing nonwoven fibers 16, which may be absorbent or nonabsorbent. The absorbent nonwoven fibers 14 may be formed from cellulose or another suitable absorbent material. Suitable cellulose fibers include without limitation fibers formed from wood, cotton, silk, straw, hay, and other plants. Rayon fibers are particularly suitable for the absorbent nonwoven fibers 14. Rayon fibers are textile filaments made from cotton linters, wood chips or other cellulose by treating them with caustic soda and carbon disulfide, and passing the resulting viscose solution through spinnerets.

When used, the reinforcing nonwoven fibers 16 may be formed from any strong, flexible polymeric material. Suitable polymeric materials include without limitation polyester, polypropylene, high density polyethylene, linear low density polyethylene, polyamides, polytetrafluoroethylene, and combinations thereof. The cloth-like nonwoven fabric 10, specifically the nonwoven fibers 12, may include about 50-100% by weight of the absorbent nonwoven fibers 14 and about 0-50% by weight of the reinforcing nonwoven fibers 16, suitably about 55-90% by weight of the absorbent nonwoven fibers 14 and about 10-45% by weight of the reinforcing nonwoven fibers 16, or about 60-80% by weight of the absorbent nonwoven fibers 14 and about 20-40% by weight of the reinforcing nonwoven fibers 16.

In accordance with the invention, the cloth-like nonwoven fabric 10 is coated with a reversible color-changing ink formation that is sensitive to the concentration of quaternary ammonium compound in the nonwoven wipe 8. On a dry weight basis, the reversible color-changing ink formulation includes about 55-98% by weight of a polymer binder, suitably about 65-96% by weight, or about 75-95% by weight. The polymer binder helps bond the nonwoven fibers 12 of the fabric 10 together, and also forms a durable bond between the nonwoven fabric 10 and the reversible color changing ink formulation. The high amount and bond strength of the binder polymer ensure that the reversible color-changing ink formulation will remain intact and functional for the useful life of the nonwoven wipe 8.

Suitable polymer binders include polyamide binders, polyurethane binders, and combinations thereof. Suitable polyamide binders include without limitation polyamides that are soluble in alcohols, acetates, and/or other organic solvents. Examples include various polyamide resins available from Arizona Chemical Co. under the trade name UNIREZ®. One such polyamide binder is UNIREZ® 2215. Suitable polyurethane binders include without limitation polyurethanes that are soluble in alcohols, acetates and/or other organic solvents. Examples include polyurethanes available from Scholle Corporation, including without limitation Scholle Solution 5110.

Other suitable polymer binders include water-dispersible polyurethanes, water-soluble acrylic polymers, and combinations thereof. An example of a suitable water-soluble polyether is a self-crosslinking aliphatic polyurethane available from Lubrizol under the trade name PERMAX® 300. An example of a suitable water soluble acrylic polymer is a self-crosslinking acrylic emulsion available from Dow Chemical Co. under the trade name RHOPLEX® E-358. These polymer binders self-crosslink during drying, after application to a nonwoven wipe 8, to provide highly durable bonding between the reversible color-changing ink formulation and the nonwoven wipe.

The reversible color-changing ink formulation also includes a reversible color-changing dye that provides acute color to the ink formulations when used in small quantities. The reversible color-changing ink formulation includes about 0.1-20% by weight of the reversible color-changing dye, suitably about 0.3-10% by weight, or about 0.5-5% by weight, based on a dry weight of the ink formulation.

Suitable reversible color-changing dyes include bromine compounds that reversibly change color at intermediate pH ranges between about 5.5 and about 8.0. One suitable bromine compound is bromothymol blue, also known as dibromothymol sulfonphthalein, having a molecular formula $C_{27}H_{28}Br_2O_5S$. Bromothymol blue reversibly changes between a blue color at pH above 7.6 and a bright yellow color at pH below 6.0. Because sanitizers containing quaternary ammonium compounds are mildly basic, a nonwoven wipe 8 of the invention treated with an ink formulation containing bromothymol blue would have a blue or green-blue color when fully charged with a quaternary ammonium sanitizing composition.

As the nonwoven wipe 8 is used and the sanitizing composition is depleted, the pH would become neutral or slightly acidic, causing the color of the nonwoven wipe 8 to change to yellow. The nonwoven wipe can then be recharged by dipping it in a solution of quaternary ammonium sanitizing composition. This recharging would cause the color of the nonwoven wipe 8 to change from yellow back to blue. This cycle of use and recharging can be repeated several times because the reversible color-changing ink formulation is durably bound to the nonwoven wipe 8 and does not separate.

The reversible color-changing ink formulation may include up to about 40% by weight of a plasticizer, suitably up to about 30% by weight, or up to about 20% by weight, based on a dry weight of the reversible color-changing ink formulation. When used, the plasticizer helps maintain the flexibility of the nonwoven wipe 8 with the reversible color-changing ink formulation applied, i.e., by softening the reversible color-changing ink formulation so that it does not stiffen the nonwoven wipe 8. Suitable plasticizers include without limitation dibutyl phthalate and triethyl citrate sold by Aldrich Chemical Co. Other suitable plasticizers include without limitation bis-(2-butoxyethyl) adipate, bis-(2-ethylhexyl) sebacate, diethyl phthalate, and combinations thereof.

The reversible color-changing ink formulation may also include up to about 30% by weight of a particulate inorganic filler, suitably about 0.5-20% by weight, or about 1-10% by weight, based on a dry weight of the reversible color-changing ink formulation. When used, the particulate inorganic filler contributes stiffness and integrity to the nonwoven wipe 8, and may provide the nonwoven wipe 8 with a more abrasive texture to facilitate scrubbing of hard surfaces. Suitable particulate inorganic fillers include without limitation silicon dioxide, calcium carbonate, clay, talc, and combinations thereof.

The reversible color-changing ink formulation may also include up to about 30% by weight of a color brightener, suitably about 0.5-20% by weight, or about 1-10% by weight, based on a dry weight of the reversible color-changing ink formulation. When used, the color brightener further enables the use of only a small amount of reversible color-changing dye by enhancing the colors of the reversible color-changing ink formulation. Suitable color brighteners include without limitation titanium dioxide, barium sulfate, and combinations thereof.

To make the reversible color-changing ink formulation, the ingredients can be mixed together in a volatile organic solvent and/or water, suitably in an amount of about 15-50% by weight ink formulation ingredients and about 50-85% by weight organic solvent and/or water. The choice of volatile organic solvents and/or water will depend largely on whether the polymer binder dissolves in the organic solvents, water, or both, as described above. Suitable volatile organic solvents include without limitation n-propyl alcohol, acetates, acetone, methylethyl ketone, toluene, tetrahydrofuran, ethyl acetate, and combinations thereof.

The reversible color-changing ink formulation can be applied to the nonwoven fabric 10 by dipping, dripping, immersion, spray coating, brush coating, roll coating, printing, or any suitable technique. The coated nonwoven fabric 10 can then be dried in the presence of heat and/or vacuum to remove the volatile organic solvent, leaving the color-changing ink composition firmly bonded to the nonwoven fabric 10. Drying temperatures of about 60° C. to about 100° C. are generally sufficient. The drying times may range from several minutes to several hours depending on the particular composition, structure and basis weight of the nonwoven fabric 10, and on the specific composition of the color-changing ink composition. The nonwoven fabric 10 can be cut and converted into individual nonwoven wipes 8 before or after the reversible color-changing ink formulation is applied.

After drying, the reversible color-changing ink composition should constitute about 0.1-10% by weight, suitably about 0.1-2% by weight of the nonwoven wipe 8. These amounts are based on the weight of the dry nonwoven wipe 8, before it is charged with a quaternary ammonium compound-based sanitizer solution.

During use, the nonwoven wipe 8 is typically charged with quaternary ammonium compound-based sanitizer solution by dipping or immersing the nonwoven wipe 8 in a cleaning bucket that contains the sanitizer solution, typically diluted with water. The nonwoven wipe 8 may also be provided as a precharged wipe which is already impregnated with quaternary ammonium compound-based sanitizer solution. One suitable quaternary ammonium compound-based sanitizer is the above-described STEPANQUAT® 2125M-P40, available from Stepan Company. Again, this product is a mixture of about 50% by weight N-alkyl (60% C14, 30% C16, 5% C12 and 5% C18) dimethyl benzyl ammonium chlorides and about 50% by weight N-alkyl (68% C12 and 32% C14) dimethyl ethyl benzyl ammonium chlorides. The product is available as a powder. For use as a sanitizing solution, the powder can suitably be added to water in an amount which results in an aqueous solution having a quaternary ammonium compound concentration of about 0.195-0.225% by weight.

The aqueous sanitizer solution is applied to the nonwoven wipe 8, as noted above, by dipping or immersing the nonwoven wipe 8 in the sanitizer solution. The amount of sanitizer solution absorbed by the nonwoven wipe 8 depends on the structural characteristics, basis weight and absorbent characteristics of the nonwoven wipe 8. The sanitizer solution may suitably contain about 180 to about 400 ppm, suitably about 180 to about 250 ppm of the quaternary ammonium compound. When fully charged, the nonwoven wipe 8 may suitably contain about 300-800% by weight, suitably about 400-600% by weight of the aqueous sanitizer solution based on the dry weight of the nonwoven wipe 8. The free quaternary ammonium compound content of the nonwoven wipe 8, based on the dry weight of the nonwoven wipe 8, may suitably be about 300 to about 1200 ppm, or about 500 ppm to about 1000 ppm. The term "free quaternary ammonium component content" refers to the amount of quaternary ammonium compound contributed by the sanitizer solution.

To determine a threshold concentration of free quaternary ammonium compound in the nonwoven wipe that causes a particular applied ink composition to change from a first color to a second color during use, the following procedure can be followed. First, the weight "D" of the dry nonwoven wipe 8 with applied ink composition is measured. Then, the nonwoven wipe 8 is impregnated with aqueous sanitizer solution and weighed, to determine the fully charged weight "C". The amount "Q" of quaternary ammonium compound in the fully charged nonwoven wipe 8 is determined by multiplying the weight ratio "R" of quaternary ammonium compound in the aqueous cleaning solution by the difference between C and D, according to the following equation:

$$Q=R(C-D)$$

The fully charged concentration "P" (in parts per million) of quaternary ammonium compound in the nonwoven wipe 8, based on the dry weight of the nonwoven wipe 8, is therefore $(Q/D) \times 10^6$.

To determine the threshold concentration of quaternary compound that triggers a color change during use, simply wipe the nonwoven wipe 8 across a table or countertop until the color begins to change from the first color to the second color, and weigh the nonwoven wipe 8 again to determine the depleted weight "L." The threshold concentration T (in parts per million) can be determined from the following equation:

$$T = P\frac{(L-D)}{(C-D)}$$

By following the foregoing procedure, different ink compositions can be tested for a particular nonwoven wipe 8 to develop an ink composition which changes color at a desired threshold concentration T. In most instances, the desired threshold concentration T for a nonwoven wipe 8 is about 180-250 ppm, suitably about 190-220 ppm. When the concentration of quaternary ammonium compound in the nonwoven wipe 8 falls below the threshold level, the nonwoven wipe 8 becomes less effective for sanitizing applications, and it becomes important to recharge the nonwoven wipe 8 with sanitizer solution.

Once the threshold concentration T has been determined for a particular ink composition, a much simpler procedure can be used to determine the relative sensitivity of different ink compositions, i.e. whether different ink compositions will change color at higher or lower levels of quaternary ammonium compound. To determine the relative sensitivity of different ink compositions, sanitizer solutions containing several different concentrations of quaternary ammonium compound can be prepared in separate buckets or containers. For example, solutions containing quaternary ammonium compounds at 0 ppm, 50 ppm, 125 ppm, 250 ppm, 500 ppm and 1000 ppm can be prepared. Then, nonwoven wipes coated with different color-changing ink compositions can each be dipped sequentially into the sanitizer solutions, beginning with the lowest concentrations, to determine the concentration of quaternary ammonium compound that triggers a color change. While this simpler procedure can be used to determine if one ink changes color at a higher or lower quaternary ammonium content relative to another ink, it will not determine the threshold concentration T of quaternary ammonium compound in a nonwoven wipe 8.

It is also within the scope of the invention to provide a method of cleaning a surface. The method includes the steps of providing a nonwoven wipe including a nonwoven fabric and a reversible color-changing ink formulation bound to the nonwoven fabric. A sanitizer solution is provided, and the nonwoven wipe is impregnated with the sanitizer solution. The surface is wiped with the nonwoven wipe until the reversible color-changing ink formulation changes from a first color indicating sufficient sanitizer solution to a second color indicating insufficient sanitizer solution. The nonwoven wipe is then impregnated with additional sanitizer solution at least until the reversible color-changing ink formulation changes back to the first color.

EXAMPLES

The following reversible color-changing ink formulations have been tested and found suitable for making the reversible color-changing nonwoven wipes of the invention. Example 1 is an organic solvent-based formulation. Example 2 is a water-based formulation. The weight percentages of the ingredients are provided on both a wet weight basis and a dry weight basis.

Example 1

| Ingredient | % By Weight (Wet Basis) | % By Weight (Dry Basis) |
|---|---|---|
| UNIREZ ® 2215 Binder | 14 | 70 |
| N-propyl alcohol | 60 | 0 |
| N-propyl acetate | 20 | 0 |
| Bromothymol blue dye | 0.5 | 2.5 |
| Triethyl citrate plasticizer | 2.5 | 12.5 |
| Silica filler | 1.0 | 5.0 |
| Titanium Dioxide Color brightener | 2.0 | 10 |
| TOTAL | 100.0 | 100.0 |

Example 2

| Ingredient | % By Weight (Wet Basis) | % By Weight (Dry Basis) |
|---|---|---|
| PERMAX ® 300 (42% solids) | 75 | 89.9 |
| Deionized water | 21.4 | 0 |
| Antifoam (Dow Corning DC 65) | 0.1 | 0.1 |
| Bromothymol blue dye | 0.5 | 1.4 |
| Silica filler | 1.0 | 2.9 |
| Titanium Dioxide color brightener | 2.0 | 5.7 |
| TOTAL | 100.0 | 100.0 |

Each of the foregoing ink formulations was mixed with the appropriate solvent to yield a proper viscosity for flexographic printing. The reversible color-changing ink formulations were printed onto nonwoven fabric substrates and dried and cured in a drying oven to yield reversible color-changing nonwoven wipes. When the reversible color-changing nonwoven wipes were immersed in an aqueous sanitizer solution containing 200 ppm or more quaternary ammonium compound, they changed from a yellow color to a greenish blue color. When the fully charged nonwoven wipes were then removed and immersed in another aqueous sanitizer solution containing less than 200 ppm quaternary ammonium compound, the nonwoven wipes changed back to a yellow color.

Aqueous solutions of 0 ppm, 100 ppm and 170 ppm quaternary ammonium compounds were tested over 100 times in the laboratory using each of the foregoing ink formulations. In each instance, the printed ink formulation changed from greenish blue to yellow when immersed in the solutions containing less than 200 ppm (±15%) of quaternary ammonium compound.

The test procedure followed was to initially print the test ink onto a selected nonwoven fabric substrate to form a wipe. Then, the printed wipes were immersed in an aqueous solution containing over 200 ppm (250-500 ppm) quaternary ammonium compound. The printed wipes were swished around in the solution by hand until the color of the printed ink became blue or greenish blue. The printed wipes were then removed, wrung out, placed into the solution containing less than 200 ppm quaternary ammonium compound, and swished around by hand until the color of the printed ink changed to yellow. The same color change occurs if the fully charged printed wipe is used to clean a hard surface until the quaternary ammonium compound falls below the threshold level.

While the embodiments of the invention described herein are exemplary, various modifications and improvements can be made without departing from the spirit and scope of the invention. The scope of the invention is indicated by the appended claims, and all changes that fall within the meaning and range of equivalents are intended to be embraced therein.

We claim:

1. A reversible color-changing polymeric article, comprising:
   a polymeric material selected from the group consisting of polyester, polypropylene, high density polyethylene, linear low density polyethylene, polyamides, polytetrafluoroethylene, and combinations thereof; and
   a dried reversible color-changing ink formulation durably bound to the polymeric material and including at least a reversible color-changing dye and a polymer binder that is not an acrylic polymer binder;
   wherein the dried reversible color-changing ink formulation enables the polymeric article to repeatedly change back and forth between a first color and a second color at a pH between about 5.5 and about 8.0 during repeated cycles of use of the polymeric article with a quaternary ammonium sanitizer solution, without separating the reversible color-changing ink formulation from the polymeric material.

2. The reversible color-changing polymeric article of claim 1, wherein the polymer binder is self-crosslinking.

3. The reversible color-changing polymeric article of claim 1, wherein the polymer binder is selected from the group consisting of polyamides, polyurethanes, and combinations thereof.

4. The reversible color-changing polymeric article of claim 1, wherein the reversible color-changing dye comprises a bromine compound.

5. The reversible color-changing polymeric article of claim 1, wherein the reversible color-changing dye comprises dibromyl sulfonphthalein.

6. The reversible color-changing polymeric article of claim 1, wherein the reversible color-changing ink formulation comprises about 55-98% by weight of the polymer binder and about 0.1-20% by weight of the reversible color-changing dye.

7. The reversible color-changing polymeric article of claim 6, wherein the reversible color-changing ink formulation further comprises a plasticizer in an amount up to about 40% by weight of the reversible color-changing ink formulation.

8. The reversible color-changing polymeric article of claim 7, wherein the plasticizer is selected from the group consisting of dibutyl phthalate, triethyl citrate, bis-(2-butoxyethyl) adipate, bis-(2-ethylhexyl) sebacate, diethyl phthalate, and combinations thereof.

9. A reversible color-changing polymeric article, comprising:
   a polymeric material selected from the group consisting of polyester, polypropylene, high density polyethylene, linear low density polyethylene, polyamides, polytetrafluoroethylene, and combinations thereof; and
   a dried reversible color-changing ink formulation durably bound to the polymeric material and including at least a reversible color-changing dye and a polymer binder that is not an acrylic polymer binder;
   wherein the dried reversible color-changing ink formulation enables the polymeric article to repeatedly change back and forth between a first color when a concentration of free quaternary ammonium compound in contact with the polymeric article exceeds a threshold concentration, and a second color when the concentration of free quaternary ammonium compound in contact with the polymeric article falls below the threshold concentration, without separating the reversible color-changing ink formulation from the polymeric article.

10. The reversible color-changing polymeric article of claim 9, wherein the threshold concentration is about 180-250 ppm.

11. The reversible color-changing polymeric article of claim 9, wherein the threshold concentration is about 190-220 ppm.

12. The reversible color-changing polymeric article of claim 9, wherein the polymer binder is self-crosslinking.

13. The reversible color-changing polymeric article of claim 9, wherein the polymer binder is selected from the group consisting of polyamides, polyurethanes, and combinations thereof.

14. The reversible color-changing polymeric article of claim 9, wherein the reversible color-changing dye comprises a bromine compound.

15. The reversible color-changing polymeric article of claim 9, wherein the reversible color-changing dye comprises dibromyl sulfonphthalein.

16. The reversible color-changing polymeric article of claim 9, wherein the reversible color-changing ink formulation comprises about 55-98% by weight of the polymer binder and about 0.1-20% by weight of the reversible color-changing dye.

17. The reversible color-changing polymeric article of claim 16, wherein the reversible color-changing ink formulation further comprises a plasticizer in an amount up to about 40% by weight of the reversible color-changing ink formulation.

18. The reversible color-changing polymeric article of claim 17, wherein the plasticizer is selected from the group consisting of dibutyl phthalate, triethyl citrate, bis-(2-butoxyethyl) adipate, bis-(2-butoxyethyl) sebacate, diethyl phthalate, and combinations thereof.

* * * * *